United States Patent [19]

Gehring et al.

[11] Patent Number: 4,804,398

[45] Date of Patent: Feb. 14, 1989

[54] 1-ARYL-4-CYANO-5-HALOGENOPYRAZOLES, COMPOSITION CONTAINING THEM, AND METHOD OF USING THEM AS SELECTIVE HERBICIDES

[75] Inventors: Reinhold Gehring, Wuppertal; Uta Jensen-Korte, Düsseldorf; Otto Schallner, Monheim; Jörg Stetter, Wuppertal; Hans-Joachim Santel, Leverkusen; Robert R. Schmidt, Bergisch Gladbach, all of Fed. Rep. of Germany

[73] Assignee: Bayer Aktiengesellschaft, Leverkusen, Fed. Rep. of Germany

[21] Appl. No.: 57,471

[22] Filed: Jun. 3, 1987

Related U.S. Application Data

[63] Continuation-in-part of Ser. No. 866,050, May 22, 1986, Pat. No. 4,747,867.

[30] Foreign Application Priority Data

Jun. 7, 1985 [DE] Fed. Rep. of Germany ....... 3520329

[51] Int. Cl.⁴ .................... A01N 43/56; C07D 231/16
[52] U.S. Cl. .................................. 71/92; 548/377
[58] Field of Search .......................... 548/377; 71/92

[56] References Cited

U.S. PATENT DOCUMENTS

| | | | |
|---|---|---|---|
| 4,496,390 | 1/1985 | Hatton et al. | 548/377 |
| 4,563,210 | 1/1986 | Beck et al. | 548/377 |
| 4,620,865 | 11/1986 | Beck et al. | 548/377 |

OTHER PUBLICATIONS

Chemical Abstracts, vol. 80, No. 13, 4/1/74, p. 341, Abstract 70749b.
Chemical Abstracts, vol. 99, No. 9, 8/29/83, Abstract 70618a.

*Primary Examiner*—Mary C. Lee
*Assistant Examiner*—Kurt G. Briscoe
*Attorney, Agent, or Firm*—Sprung Horn Kramer & Woods

[57] ABSTRACT

Herbicidally active novel 1-phenyl-4-cyano-5-halogenopyrazoles of the formula

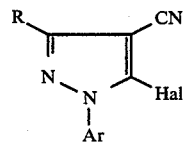

in which
 R is hydrogen or alkyl,
 Hal is halogen, and
 Ar is phenyl substituted at least once by a radical other than halogen.

Intermediates of the formulas

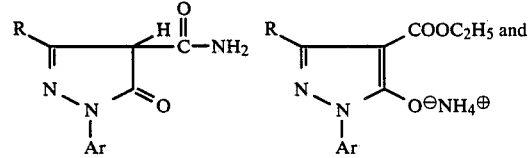

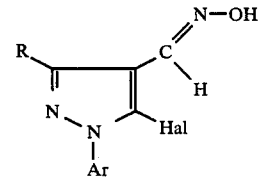

are also new.

7 Claims, No Drawings

1-ARYL-4-CYANO-5-HALOGENOPYRAZOLES, COMPOSITION CONTAINING THEM, AND METHOD OF USING THEM AS SELECTIVE HERBICIDES

This is a continuation-in-part of Application Ser. No. 866,050, filed May 22, 1986, now U.S. Pat. No. 4,747,867.

The invention relates to new 1-aryl-4-cyano-5-halogenopyrazoles, several processes for their preparation and their use as herbicides.

It is already known that 1-aryl-4-cyanopyrazoles, such as, for example, 4-cyano-5-propionamide-1-(2,4,6-trichlorophenyl)-pyrazole, possess herbicidal properties, in particular selective herbicidal properties (see, for example DE-OS (German Published Specification) No. 3,226,513).

However, the herbicidal activity of these previously known compounds with respect to weeds, as well as their toloration by important crop plants, is not always completely satisfactory in all fields of use.

New 1-aryl-4-cyano-5-halogenopyrazoles of the general formula (I)

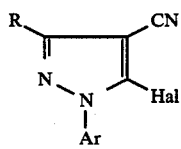  (I)

in which
R represents hydrogen or alkyl,
Hal represents halogen and
Ar represents phenyl substituted at least once by a radical other than halogen, have been found.

It has also been found that the new 1-aryl-4-cyano-5-halogenopyrazoles of the general formula (I)

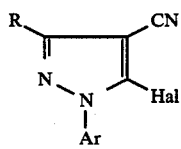  (I)

in which
R represents hydrogen or alkyl,
Hal represents halogen and
Ar represents phenyl substituted at least once by a radical other than halogen,
are obtained when
(a-α) pyrazolinones of the formula (II)

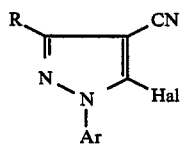  (II)

in which
R and Ar have the meaning given above,
or
(a-β) ammonium 5-hydroxypyrazole salts of the formula (III)

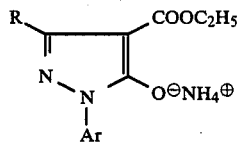  (III)

in which
R and Ar have the meaning given above, are reacted with phosphorus oxyhalides of the formula (IV)

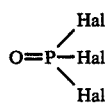  (IV)

in which
Hal has the meaning given above,
or when
(b) 4-hydroximinomethyl-pyrazoles of the formula (V)

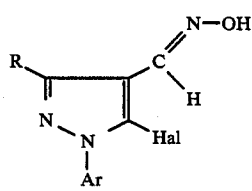  (V)

in which
R, Hal and Ar have the meaning given above, are reacted with acetic anhydride, if appropriate in the presence of a diluent,
or when
(c) 5-amino-4-cyano-pyrazoles of the formula (VI)

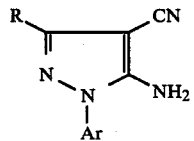  (VI)

in which
R and Ar have the meaning given above, are reacted with sodium nitrite in the presence of a hydrohalic acid of the formula (VII)

  H-Hal  (VII)

in which
Hal has the meaning given above, if appropriate in the presence of a diluent,
or when
(d) the 1-aryl-4-cyano-5-halogenopyrazoles of the formula (I)

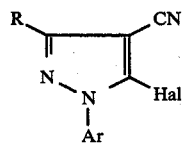  (I)

in which

R, Hal and Ar have the meanings given above, which are obtainable by process (a), (b), or (c), are reacted with halides of the formula (VIII)

$$M^{\oplus} (Hal^{\ominus})^1 \quad \quad (VIII)$$

in which

M$^{\oplus}$ represents one equivalent of a metal cation or represents an optionally substituted ammonium ion, and (Hal$^{\ominus}$)$^1$ represents a halide anion but differs from Hal, if appropriate in the presence of a diluent and, if appropriate in the presence of a phase-transfer catalyst.

In this way, the corresponding halogen derivatives of the 1-aryl-4-cyano-5-halogenopyrazoles of the formula (I) in which, for example, chlorine is replaced with iodine are obtained from a particular halogen derivative of the 1-aryl-4-cyano-5-halogenopyrazoles of the formula (I), for example the chlorine derivative, by transhalogenation, for example with sodium iodide.

Finally, it has been found that the new 1-aryl-4-cyano-5-halogenopyrazoles of the general formula (I) possess herbicidal properties, in particular selective herbicidal properties.

Surprisingly, the 1-aryl-4-cyano-5-halogenopyrazoles according to the invention, of the formula (I), possess a comparable general herbicidal activity against weeds which are difficult to combat, coupled with a substantially improved selectivity for crop plants, in comparison with the 1-aryl-4-cyanopyrazoles, such as, for example, 4-cyano-5-propionamido-1-(2,4,6-trichlorophenyl)-pyrazol, which are known from the prior art and are similar compounds chemically and in terms of their action.

In the general formulae, alkyl radicals R represent alkyl having 1 to 4 carbon atoms, in particular alkyl having 1 or 2 carbon atoms, such as methyl, ethyl, n- and i-propyl, or n-, i-, sec.- and t-butyl. In the general formulae, R very particularly preferably represents hydrogen or methyl.

In the general formulae, Hal represents fluorine, chlorine, bromine or iodine, in particular fluorine, chlorine or bromine, very particularly preferably chlorine or bromine.

In the general formulae, Ar represents phenyl which is monosubstituted or polysubstituted by identical or different substituents, as qualified hereinabove, suitable substituents being: alkyl preferably having 1 to 4, in particular 1 or 2, carbon atoms, such as methyl, ethyl, n- and i-propyl, n-, i-, sec.- and t-butyl; alkoxy preferably having 1 to 4, in particular 1 or 2, carbon atoms, such as methoxy, ethoxy, n- and i-propoxy, n-, i-, sec.- and t-butoxy; alkoxycarbonyl preferably having 2 to 4, in particular 2 or 3, carbon atoms, such as methoxycarbonyl, ethoxycarbonyl or propoxycarbonyl; halogenoalkyl preferably having 1 to 4, in particular 1 or 2, carbon atoms and preferably 1 to 9, in particular 1 to 5 and very particularly preferably 1 to 3, halogen atoms, the halogen atoms being identical or different and being fluorine, chlorine, bromine or iodine, in particular fluorine, chlorine or bromine, very particularly fluorine or chlorine; halogenoalkoxy preferably having 1 to 4, in particular 1 or 2, carbon atoms and preferably 1 to 9, in particular 1 to 5, very particularly 1 to 3, halogen atoms, the halogen atoms being fluorine, chlorine, bromine or iodine, in particular fluorine, chlorine or bromine and very particularly fluorine or chlorine; halogen, preferably fluorine, chlorine, bromine or iodine, in particular fluorine, chlorine or bromine, very particularly chlorine or bromine; cyano or nitro.

In the case where Ar represents phenyl which is substituted by the radical $-S(O)_n-R^1$, $R^1$ represents alkyl having 1 to 4, in particular 1 or 2, carbon atoms, such as methyl, ethyl, n- and i-propyl, n-, i-, sec.- and t-butyl; alkylamino having 1 to 4, in particular 1 or 2, carbon atoms, such as methylamino, ethylamino, propylamino or butylamino; dialkylamino having 1 to 4, in particular 1 or 2, carbon atoms in the individual alkyl parts, such as dimethylamino, diethylamino, dipropylamino or dibutylamino; halogenoalkyl having 1 to 4, in particular 1 or 2, carbon atoms and 1 to 9, in particular 1 to 5, very particularly 1 to 3, halogen atoms, the halogen atoms being identical or different and being fluorine, chlorine, bromine or iodine, particularly fluorine, chlorine or bromine, very particularly fluorine or chlorine, such as trifluoromethyl; and n represents 0, 1 or 2.

Formula (I) gives a general definition of the 1-aryl-4-cyano-5-halogenopyrazoles according to the invention.

Preferred compounds of the formula (I) are those in which

R represents hydrogen or straight-chain or branched alkyl having 1 to 4 carbon atoms, Hal represents halogen and Ar represents phenyl which is monosubstituted or polysubstituted by identical or different substituents, as qualified, suitable substituents being:

cyano, nitro, halogen, alkyl, alkoxy or alkoxycarbonyl, each of which is straight-chain or branched and each of which has up to 4 carbon atoms, halogenoalkyl or halogenoalkoxy, each of which is straight-chain or branched and each of which has up to 4 carbon atoms and up to 9 identical or different halogen atoms, or the radical $-S(O)_n-R^1$, wherein $R^1$ represents amino, alkyl, alkylamino, dialkylamino or halogenoalkyl, each of which is straight-chain or branched and each of which has up to 4 carbon atoms in the individual alkyl parts and, in the case of halogenoalkyl, up to 9 identical or different halogen atoms, and n represents a number 0, 1 or 2.

Particularly preferred 1-aryl-4-cyano-5-halogenopyrazoles of the general formula (I) are those in which R represents hydrogen, methyl or ethyl, Hal represents fluorine, chlorine, bromine or iodine, and Ar represents phenyl which is monosubstituted or disubstituted to pentasubstituted by identical or different substituents, as qualified, suitable substituents being:

cyano, nitro, fluorine, chlorine, bromine, iodine, methyl, ethyl, n- and i-propyl, n-, i-, s- and t-butyl, methoxy, ethoxy, methoxycarbonyl, ethoxycarbonyl, trifluoromethyl, trichloromethyl, dichlorofluoromethyl, difluorochloromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, dichloroethoxy, pentachloroethoxy or the radical —S(O)$_n$-R$^1$,
wherein
R$^1$ represents amino, methylamino, ethylamino, dimethylamino, diethylamino, fluorodichloromethyl, difluoromethyl, tetrafluoroethyl, trichloroethyl, trifluoromethyl, methyl, or ethyl, and
n represents a number 0, 1 or 2.

In addition to the compounds mentioned in the preparation examples, the following 1-aryl-4-cyano-5-halogenopyrazoles of the general formula (I) may be mentioned individually:

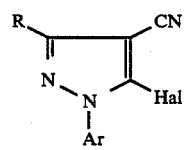
(I)

TABLE 1

| R | Hal | Ar |
|---|-----|----|
| H | Cl | 4-CF$_3$-C$_6$H$_4$ |
| H | Cl | 3,5-bis(CF$_3$)-C$_6$H$_3$ |
| H | Cl | 3,5-Cl$_2$-4-OCF$_3$-C$_6$H$_2$ |
| H | Br | 3-Cl-4-CF$_3$-C$_6$H$_3$ |
| H | Br | 3,5-Cl$_2$-4-CF$_3$-C$_6$H$_2$ |
| H | Cl | 3-Cl-4-CF$_3$-C$_6$H$_3$ |
| H | Cl | 3,5-Cl$_2$-4-OCF$_3$-C$_6$H$_2$ |

TABLE 1-continued

| R | Hal | Ar |
|---|-----|----|
| H | Cl | 3,5-Cl$_2$-4-SCF$_3$-C$_6$H$_2$ |
| H | Cl | 3-Cl-4-SCF$_3$-C$_6$H$_3$ |
| H | Br | 3-Cl-4-SO$_2$CF$_3$-C$_6$H$_3$ |
| H | Br | 3,5-Cl$_2$-4-SO$_2$CF$_3$-C$_6$H$_2$ |
| H | Br | 3,5-Cl$_2$-4-SOCF$_3$-C$_6$H$_2$ |
| H | Cl | 3-Cl-4-CF$_3$-C$_6$H$_3$ |
| H | Cl | 2,3,5-Cl$_3$-4-CF$_3$-C$_6$H |
| H | Cl | 3,5-Cl$_2$-4-OCF$_3$-C$_6$H$_2$ |
| H | Cl | 2,3,5-Cl$_3$-4-OCF$_3$-C$_6$H |

TABLE 1-continued
| R | Hal | Ar |
|---|---|---|
| H | Cl | 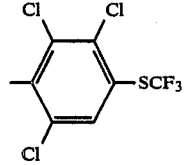 |
| H | Br | 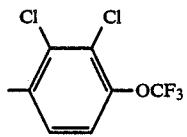 |
| H | Br | 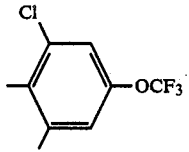 |
| H | Br | 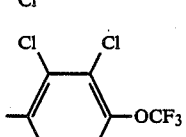 |
| H | Br | 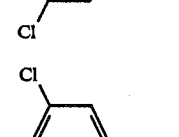 |
| H | Br | 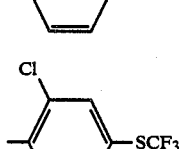 |
| H | Br | 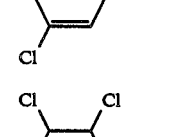 |
| H | Cl | 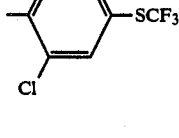 |
| H | Br | 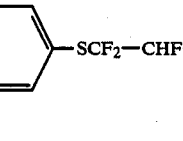 |
| CH$_3$ | Cl | 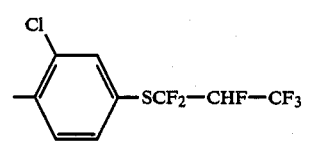 |
| CH$_3$ | Cl | 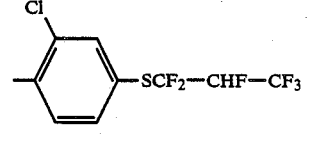 |
| CH$_3$ | Br | 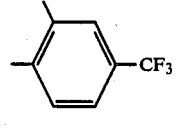 |
| CH$_3$ | Br |  |
| H | Cl | 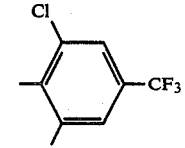 |
| H | Cl | 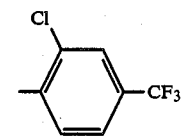 |
| H | Br | 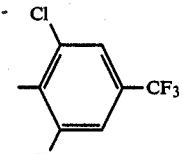 |
| H | Cl | 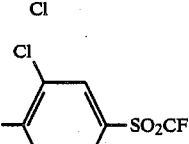 |
| CH$_3$ | Cl | 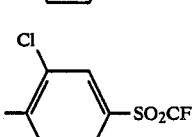 |
| CH$_3$ | Cl | 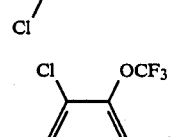 |
| CH$_3$ | Cl | 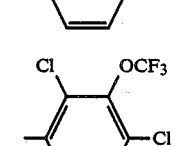 |

TABLE 1-continued

| R | Hal | Ar |
|---|---|---|
| CH3 | Br | 3-Cl, 4-OCF3 phenyl |
| CH3 | Br | 3,5-diCl, 4-OCF3 phenyl |
| CH3 | Cl | 2,3,5-triCl, 4-CF3 phenyl |
| CH3 | Br | 2,3-diCl, 4-CF3 phenyl |
| CH3 | Cl | 3-Cl, 4-OCF3 phenyl |
| CH3 | Cl | 3,5-diCl, 4-OCF3 phenyl |
| CH3 | Cl | 2,3,5-triCl, 4-OCF3 phenyl |
| CH3 | Br | 3-Cl, 4-SCF3 phenyl |
| CH3 | Br | 3,5-diCl, 4-SCF3 phenyl |
| CH3 | Br | 2,3,5-triCl, 4-SCF3 phenyl |
| CH3 | Cl | 3-Cl, 4-SO2CF3 phenyl |
| CH3 | Br | 2,5-diCl, 4-SO2CF3 phenyl |
| CH3 | Cl | 3,5-diCl, 4-SO2CF3 phenyl |
| CH3 | Br | 3-Cl, 4-SO2CF3 phenyl |

If, for example, 1-(2-chloro-4-trifluoromethyl-phenyl)-Δ²-(1H)-pyrazolin-5-one-4-carboxamide and phosphorus oxybromide are used as starting materials, the course of the reaction of process (a-α) according to the invention can be represented by the following equation:

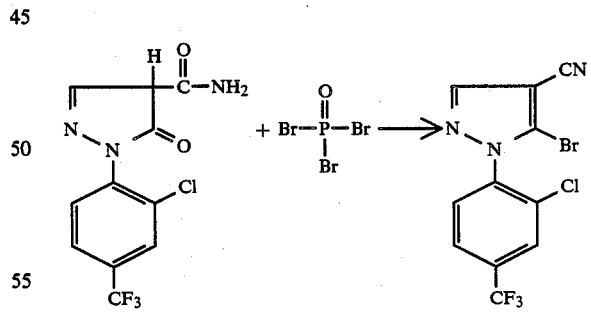

If, for example, the ammonium salt of 1-(2-chloro-4-trifluoromethyl-phenyl)-4-ethoxycarbonyl-5-hydroxypyrazole and phosphorus oxychloride are used as starting materials, the course of the reaction of process (a-β) according to the invention can be represented by the following equation:

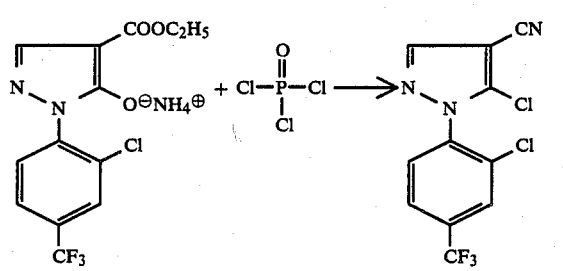 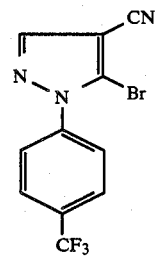

If, for example, 5-chloro-1-(2,6-dichloro-4-trifluoromethylphenyl)-4-hydroximinomethyl-pyrazole and acetic anhydride are used as starting materials, the course of the reaction of process (b) according to the invention can be represented by the following equation:

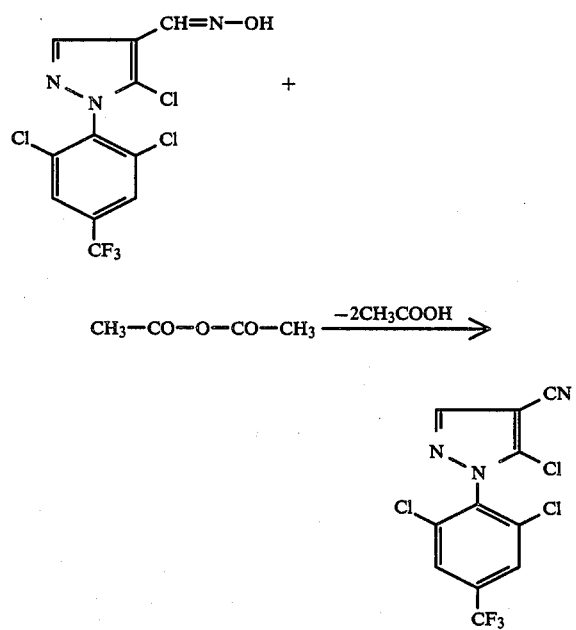

If, for example, 5-amino-4-cyano-1-(4-trifluoromethylphenyl)-pyrazole and sodium nitrite are used in the presence of hydrobromic acid as starting materials, the course of the reaction of process (c) according to the invention can be represented by the following equation:

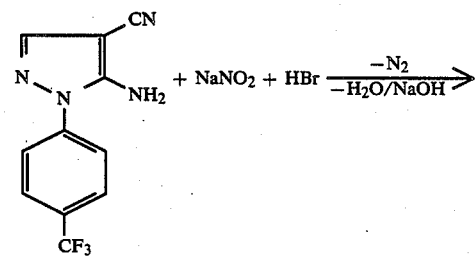

If, for example, 5-chloro-4-cyano-1-(2-chloro-4-trifluoromethylphenyl)-pyrazole and sodium fluoride are used as starting materials, the course of the reaction of process (d) according to the invention can be represented by the following equation:

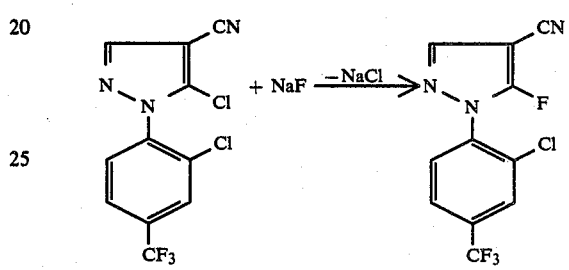

Formula (II) gives a general definition of the pyrazolinones required as starting materials for carrying out process (a-α) according to the invention. In this formula (II), R and Ar preferably represent those radicals which have already been mentioned in connection with the description of the substances according to the invention, of the formula (I), as being preferred for this substituent.

The pyrazolinones of the formula (II) were hitherto unknown. They are obtained when 4-ethoxycarbonyl-pyrazolin-5-ones of the formula (IX)

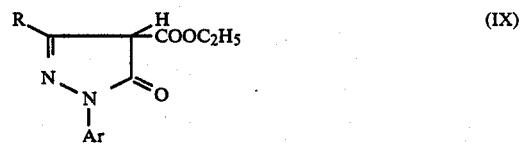

in which
R represents hydrogen or alkyl and
Ar represents substituted phenyl, as qualified,
are reacted with ammonia in the presence of a diluent, such as, for example, ethanol, at temperatures between 80° C. and 200° C.,
or when pyrazolin-5-ones of the formula (X)

in which
R represents hydrogen or alkyl and
Ar represents substituted phenyl, as qualified, are reacted with urea, if appropriate in the presence of a diluent, such as, for example, ethanol, at temperatures between 100° C. and 250° C.

Formula (III) gives a general definition of the ammonium 5-hydroxypyrazole salts required as starting materials for carrying out process (a-β) according to the invention. In this formula (III), R and Ar preferably represent those radicals which have already been mentioned in connection with the description of the substances according to the invention, of the formula (I), as being preferred for these substituents.

The ammonium 5-hydroxypyrazole salts of the formular (III) were likewise hitherto unknown. They are obtained when 4-ethoxycarbonylpyrazolin-5-ones of the formula (IX)

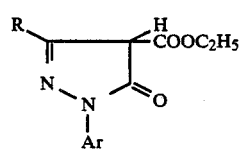

in which
R and Ar have the meaning given above,
which are in equilibrium with the tautomeric form of the formula (IX a)

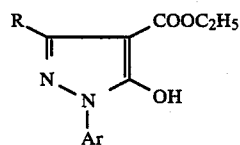

in which
R and Ar have the meaning given above,
are reacted with aqueous ammonia at temperatures between 20° C. and 100° C.

Formula (IV) gives a general definition of the phosphorus oxyhalides furthermore required as starting materials for carrying out process (a) according to the invention. In this formula (IV) Hal preferably represents those radicals which have already been mentioned in connection with the description of the substances according to the invention, of the formula (I), as being preferred for this substituent.

The phosphorus oxyhalides of the formula (IV) are generally known compounds of organic chemistry.

The 4-etnoxycarbonyl-pyrazolin-5-ones of the general formula (IX) are known (see U.S. Pat. No. 4,260,751; Tetrahedron 33, 2829–2836 (1977)) or can be obtained in a simple analogous manner by methods which are known in principle.

The pyrazolin-5-ones of the formula (X) are likewise known (see, for example, Czechoslovakian Pat. Nos. 154,959 of 15.9.1974, J. Ind. Chem. Soc. 52, 168 (1975) or French Pat. Nos. 1,516,959 of 15.3.1968), or can be obtained in a simple manner by known methods.

Formula (V) gives a general definition of the 4-hydroximinomethylpyrazoles required as starting materials for carrying out process (b) according to the invention. In this formula (V), R, Ar and Hal preferably represent those radicals which have already been mentioned in connection with the description of the substances according to the invention, of the formula (I), as being preferred for these substituents.

The 4-hydroximinomethyl-pyrazoles of the formula (V) were hitherto unknown. They are obtained when pyrazolin-5-ones of the formula (X)

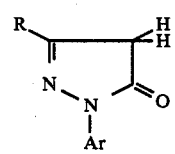

in which
R and Ar have the meaning given above,
or when 5-halogenopyrazoles of the formula (XI)

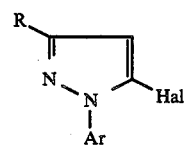

in which
R and Ar have the meaning given above and
Hal represents halogen,
are reacted with a phosphorus oxyhalide of the formula (IV)

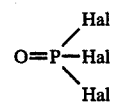

in which
Hal has the meaning given above,
and a suitable formamide of the formula (XII)

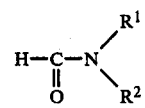

in which
$R^1$ represents alkyl, in particular methyl or ethyl, and
$R^2$ represents alkyl or aryl, in particular methyl, ethyl or phenyl,
at temperatures between 50° C. and 150° C., by methods which are known in principle ("Vilsmeier formylation"), and the resulting 4-formyl-5-halogeno-pyrazoles of the formula (XIII)

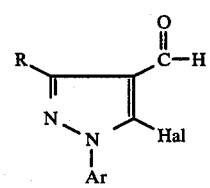

in which
R, Ar and Hal have the meaning given above, are reacted with hydroxylamine, if appropriate in the presence of a diluent, such as, for example, ethanol, at temperatures between 20° C. and 150° C.

The 5-halogenopyrazoles of the formula (XI) are obtained when pyrazolin-5-ones of the formula (X)

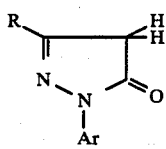

in which
R and Ar have the meaning given above, are reacted with a phosphorus oxyhalide of the formula (IV)

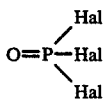

in which
Hal has the meaning given above, at temperatures between 100° C. and 25020 C.

Formula (VI) gives a general definition of the 5-amino-4-cyano-pyrazoles required as starting materials in carrying out process (c) according to the invention.

In this formula (VI), R and Ar preferably represent those radicals which have already been mentioned in connection with the description of the substances according to the invention, of the formula (I), as being preferred for these substituents.

Some of the 5-amino-4-cyano-pyrazoles of the formula (VI) are known (see, for example, European Pat. No. 34,945; DE-OS (German Published Specification) No. 3,226,496; DE-OS (German Published Specification) No. 3,129,429 or U.S. Ser. No. 659,731 filed Oct. 11, 1984 now pending; or they can be obtained in a similar manner by known methods in which, for example, ethoxymethylenemalodinitrile of the formula (XIV)

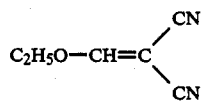

is either reacted with arylhydrazines of the formula (XV)

in which
Ar has the meaning given above,
in a first stage, if appropriate in the presence of a diluent, such as, for example, glacial acetic acid or ethanol, and, if appropriate, in the presence of a reaction auxiliary, such as, for example, sodium acetate, at temperatures between −20° C. and +20° C. to give the arylhydrazine derivatives of the formula (XVI)

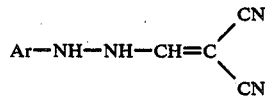

in which
Ar has the meaning given above,
and, in a 2nd stage, these cyclized, if appropriate in the presence of a diluent, such as, for example, ethylene glycol monoethyl ether, at temperatures between +50° C. and +150° C., or directly cyclized directly in one reaction step without isolation of the intermediate of the formula (XVI), if appropriate in the presence of a diluent, such as, for example, ethylene glycol monoethyl ether or ethanol, at temperatures between +50° C. and +150° C.

Ethoxymethylenemalodinitrile of the formula (XIV) and the arylhydrazines of the formula (XV) are known, or can be prepared in a simple analogous manner by known methods (see, for example, Houben-Weyl "Methoden der organischen Chemie" (Methods of Organic Chemistry), volume X/2, page 203, Thieme Verlag Stuttgart, 1967), U.S. Pat. Nos. 4,127,575; 3,609,158; DE-OS (German Published Specification) No. 2,558,399 or J. Chem. Soc. C 167–174 (1971).

Formula (VII) gives a general definition of the hydrohalic acids furthermore required as starting materials for carrying out process (c) according to the invention. In this formula (VII), Hal preferably represents those radicals which have already been mentioned in connection with the description of the substances according to the invention, of the formula (I), as being for this substituent.

The hydrohalic acids of the formula (VII) are generally known compounds.

Formula (I) gives a general definition of the 1-aryl-4-cyano-5-halogeno-pyrazoles required as starting materials for carrying out process (d) according to the invention.

The 1-aryl-4-cyano-5-halogenopyrazoles of the formula (I) are compounds according to the invention and can be obtained with the aid of processes (a), (b) or (c) according to the invention.

Formula (VII) gives a general definition of the halides furthermore required as starting materials for carrying out process (d) according to the invention. In this formula (VIII), $M^+$ preferably represents a sodium or potassium cation or an ammonium or tetraalkylammonium ion. Suitable alkyl radicals being those having 1 to 12 carbon atoms. $(Hal^-)^1$ preferably represents fluorine, chlorine, bromine or iodine.

The halides of the formula (VIII) are likewise generally known compounds of organic chemistry.

Processes (a-α) and (a-β) are generally carried out without the addition of a diluent. As a rule, an appropriate excess of phosphorus oxyhalide serves as the solvent.

In carrying out processes (a-α) and (a-β) according to the invention, the reaction temperatures can be varied within a relatively wide range. In general, the reaction is carried out at between +50° C. and +200° C, preferably between +100° C. and +180° C.

To carry out processes (a-α) and (a-β) according to the invention, 1 to 20 mols, in particular 1 to 10 mols, of a phosphorus oxyhalide of the formula (IV) are generally employed per mol of pyrazolinone of the formula (II) or ammonium 5-hydroxypyrazol salt of the formula (III).

If the boiling point of the phosphorus oxyhalide used is below the required reaction temperature, it may be necessary to employ pressure. In this case, the reaction mixture is sealed in a bomb tube or autoclave and heated for several hours at the required reaction temperature. To work up the reaction mixture, it is neutralized with aqueous carbonate solution and filtered under suction. The 1-aryl-4-cyano-5-halogenopyrazole of the formula (I) can be extracted from the residue using a suitable organic solvent.

Suitable diluents for carrying out the process (b) according to the invention are inert organic solvents which are defined in detail further below. However, an appropriate excess of the acetic anhydride simultaneously used as a reagent is preferably employed as the solvent.

In carrying out process (b) according to the invention, the reaction temperatures can be varied within a relatively wide range. In general, the reaction is carried out at between 50° C. and 180° C., preferably between 80° C. and 150° C.

To carry out process (b) according to the invention, 1 to 20 mols, in particular 1 to 10 mols, of acetic anhydride are generally employed per mol of 4-hydroxyiminomethyl-pyrazole of the formula (V). The reaction procedure, working up and isolation of the reaction products of the formula (I) are carried out analogously to known methods (see, for example, Zh. org. Khim. 9, 2416-2421 (1973)).

Suitable diluents for carrying out process (c) according to the invention are all solvents which are customarily used for such diazotization reactions, such as, for example, acetic acid. An excess of the hydrohalic acid of the formula (VII) which is employed as a reactant is preferably also used as the diluent.

In carrying out process (c) according to the invention, the reaction temperatures can be varied within a relatively wide range. In general, the reaction is carried out at temperatures between $-20°$ C. and $+120°$ C., preferably at temperatures between $-10°$ C. and $+80°$ C.

To carry out process (c) according to the invention, 1 to 10 mols of sodium nitrite and 1 to 100 mols of the hydrohalic acid of the formula (VII) are generally employed per mol of 5-amino-4-cyanopyrazole of the formula (VI). The reaction procedure, working up and isolation of the reaction products are carried out analogously to known methods (see, for example, "Organikum" (Organic Chemistry) 15th edition; VEB Deutscher Verlag der Wissenschaften, Berlin 1981, page 652 et seq.).

Suitable diluents for carrying out process (d) according to the invention are inert organic solvents.

These include, in particular, aliphatic and aromatic, optionally halogenated hydrocarbons, such as, for example, benzine, benzene, toluene, xylene, chlorobenzene, petroleum ether, hexane, cyclohexane, dichloromethane, chloroform or carbon tetrachloride, ethers, such as diethyl ether, dioxane, tetrahydrofuran or ethylene glycol dimethyl or diethyl ether, ketones, such as acetone or butanone, nitriles, such as acetonitrile or propionitrile, amides, such as dimethylformamide, dimethylacetamide, N-methylformamide, N-methylpyrrolidone or hexamethylphosphoric acid triamide, esters, such as ethyl acetate, sulphoxides and sulphones, such as dimethyl sulphoxide, or sulpholane, and alcohols, such as methanol, ethanol or propanol.

Suitable catalysts for carrying out process (d) according to the invention are quaternary ammonium or phosphonium salts or cyclic polyethers.

The following may be mentioned as examples of such catalysts: tetrabutylammonium iodide, tetrabutylammonium bromide, tributylmethylphosphonium bromide, trimethyl-$C_{13}/C_{15}$-alkylammonium chloride, dibenzyl-dimethylammonium methylsulphate, dimethyl-$C_{12}/C_{14}$-alkyl-benzylammonium chloride, tetrabutylammonium hydroxide, 18-crown-6, triethylbenzylammonium chloride and trimethylbenzylammonium chloride.

In carrying out process (d) according to the invention, the reaction temperature can be varied within a relatively wide range. It is in general between 0° C. and $+120°$ C., preferably between $+20°$ C. and $+80°$ C.

To carry out process (d) according to the invention, 1 to 50 mols, preferably 1 to 20 mols, of the halide of the formula (VIII) and 0.01 to 1 mol of a phase-transfer catalyst are generally employed per mol of the starting compound of the formula (Ia). The reaction procedure, working-up and isolation of the reaction products are carried out analogously to known processes (see, for example, "Organikum" (Organic Chemistry), 15th edition, VEB Deutscher Verlag der Wissenschaften, Berlin 1981, page 421 et seq.).

In addition to their use as herbicidal active compounds, the compounds according to the invention, of the formula (I), can also be used as intermediate products for the synthesis of further active compounds. They can be reacted with, for example, amines to give the corresponding 5-amino-1-aryl-4-cyanopyrazoles, which likewise possess herbicidal activity and which form the subject of EP-OS (European Published Specification) No. 34,945, DE-OS (German Published Specification) No. 3,226,496 DE-OS (German Published Specification) No. 3,129,429, and U.S. Ser. No. 659,731, filed Oct. 11, 1984, now U.S. Pat. No. 4,668,280.

The active compounds according to the invention can be used as defoliants, desiccants and agents for destroying broad-leaved plants and especially as weed-killers. By weeds, in the broadest sense, there are to be understood all plants which grow in locations where they are undesired.

Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, LIndernia, Lamium, Veronica, Abutilon, Emex, Datura, Viola, Galeopsis, Papaver and Centaurea.

Dicotyledon cultures of the genera: Gossypium, Glycine, Beta, Dauous, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

In addition to possessing a particularly good general herbicidal activity, the active compounds according to the invention, of the formula (I), also exhibit a substantially improved plant toleration in important cultures, and can be employed as selective weed-combating agents both in dicotyledon cultures, such as, for example, sugar beet, cotton plantations, soy beans or groundnuts, and in mono-cotyledon cultures, in particular cereals, such as, for example, wheat or corn.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compounds, and very fine capsules in polymeric substances.

These formulations are produced in known manner, for example by mixing the active compounds with extenders, that is, liquid solvents and/or solid carriers, optionally with the use of surface-active agents, that is, emulsifying agents and/or dispersing agents, and/or foam-forming agents.

In the case of the use of water as an extender, organic solvents can, for example, also be used as auxiliary solvents. As liquid solvents, there are suitable in the main: aromatics, such as oxylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylenefatty alcohol ethers, for example alkylaryl polyglycol ethers, alkylsulphonates, alkylsulphates, arylsulphonates as well as albumin hydrolysis products; as dispersing agents there are suitable: for example Ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients, such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used, for combating weeds, as mixtures with known herbicides, finished formulations or tank mixtures being possible.

Suitable herbicides for the mixtures are known herbicides, such as, for example, 1-amino-6-ethylthio-3-(2,2-dimethylpropyl)-1,3,5-triazine-2,4-(1H,3H)-dione or or N-(2-benzothiazolyl)-N,N'-dimethyl-urea, for combating weeds in cereals; 4-amino-3-methyl-6-phenyl-1,2,4-triazin-5(4H)-one for combating weeds in sugar beet, and 4-amino-6-(1,1-dimethylethyl)-3-methylthio-1,2,4-triazin-5(4H) one for combating weeds in soy beans.

Mixtures with N,N-dimethyl-N'-(3,chloro-4-methylphenyl)-urea; N,N-dimethyl-N'-(4-isopropylphenyl)-urea; 4-amino-6-t-butyl-3-ethylthio-1,2,4-triazin-5(4H)-one, 2,4-dichlorophenoxyacetic acid; 2,4-dichlorophenoxypropionic acid; (2-methyl-4-chlorophenoxy)-acetic acid; (4-chloro-2-methylphenoxy-propionic acid; chloroacetic acid N-(methoxymethyl)-2,6-diethylanilide; 2-ethyl-6-methyl-N-(1-methyl-2-methoxyethyl)-chloroacetanilide; 2-benzyloxyethyl, trimethylsilylmethyl or 2,2-diethoxyethyl 2-[4-(3,5-dichloropyrid-2-yloxy)-phenoxy]-propionate; methyl 5-(2,4-dichlorophenoxy)-2-nitrobenzoate; 3,5-diiodo-4-hydroxybenzonitrile; 3-isopropyl-2,1,3-benzothiadiazin-4-one-2,2-dioxide; 2-chloro-N-<[(4-methoxy-6-methyl-1,3,5-triazin-2-yl)-amino]-carbonyl>-benzenesulphonamide; N-methyl-2-(1,3-benzothiazol-2-yloxy)-acetanilide; 2-<4-[(3-chloro-5-(trifluoromethyl)-2-pyridinyl)-oxy]-phenoxy>-propionic acid or ethyl 2-<4-[(3-chloro-5-(trifluoromethyl)-2-pyridinyl)-oxy]-phenoxy>-propionate; S-(2,3,3-trichloroallyl) N,N-diisopropyl-thiocarbamate; 5-(2-chloro-4-trifluoromethylphenoxy)-2-nitrobenzoic acid; 5-(2-chloro-4-trifluoromethylphenoxy)-N-methylsulphonyl-2-nitrobenzamide and 2-chloro-4-ethylamino-6-isopropylamino-1,3,5-triazine are also advantageous.

Some mixtures surprisingly also exhibit a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil area, preferably between 0.05 and 5 kg per ha.

The preparation and the use of the active compounds according to the invention are described in the examples below.

EXAMPLE 1

Process a-β

(a)

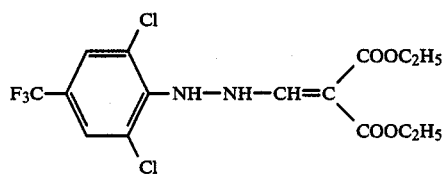

24.5 g (0.1 mol) of 2,6-dichloro-4-trifluoromethylphenyl hydrazine and 21.6 g (0.1 mol) of diethyl ethoxymethylene malonate are stirred for 24 hours at room temperature in 150 ml of ethyl alcohol, the solvent removed by vacuum, and the crystalline residue stirred with petroleum ether. Suctioning off and air-drying results in a yield of 33 g (79.5% of the theoretical) of N-[2,2-bis-(ethoxy-carbonyl)-vinyl]-N'-(2,6-dichloro-4-trifluoromethylphenyl) hydrazine with a melting point of 86° C.

(b)

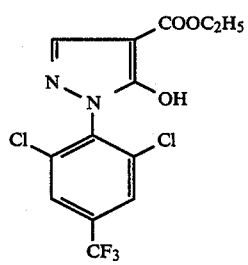

31.1 g (0.075 mol) of N-[2,2-bis-(ethoxycarbonyl)-vinyl]-N'-(2,6-dichloro-4-trifluoromethylphenyl)-hydrazine are heated slowly to 170° C. and stirred for 45 minutes at 170°-175° C., with 8 ml of ethyl alcohol simultaneously being distilled off and the residue slowly becoming solid. The resulting residue is stirred with acetonitrile and suctioned off. The yield is 17 g (61.4% of the theoretical) of 4-ethoxycarbonyl-5-hydroxy-1-(2,6-dichloro-4-trifluoro-methyl)-pyrazole with a melting point of 213°C.

(c)

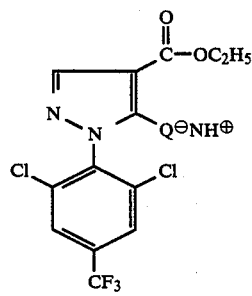

110.7 g (0.3 mol) of 4-ethoxycarbonyl-5-hydroxy-1-(2,6-dichloro-4-trifluoromethylphenyl)-pyrazole are heated to the boiling point in 2000 ml of 25% liquid ammonia, hot-filtered, and cooled to room temperature. The precipitate is filtered out and air-dried. The yield is 89 g (76.9% of the theoretical) of 4-ethoxycarbonyl-5-hydroxy-1-(2,6-dichloro-4-trifluoromethyl-phenyl)-pyrazole ammonium salt with a melting point of 148° C.

(d)

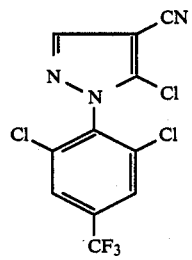

A mixture of 38.6 g (0.1 mol) of 4-ethoxycarbonyl-5-hydroxy-1-(2,6-dichloro-4-trifluoromethylphenyl)-pyrazole ammonium salt and 75 ml (0.8 mol) of phosphorus oxychloride is heated to 160° C. for 15 hours in the autoclave. The reaction mixture is cooled and dripped at room temperature into an aqueous solution of potassium carbonate and stirred for 10 minutes subsequent to termination of addition, and the precipitate is suctioned off. The solid residue is extracted over several days with petroleum ether and the petroleum ether phase vacuum concentrated. The yield is 11 g (32.4% of theoretical) of 5-chloro-4-cyano-1-(2,6-dichloro-4-trifluoromethyl)-pyrazole with a melting point of 68°-72° C.

A 1-g sample recrystallized from petroleum ether (by dissolving in 7 ml of hot petroleum ether, cooling to −20° C., and suctioning off the precipitate) has a melting point of 86°-87° C.

EXAMPLE 2

Process b (a)

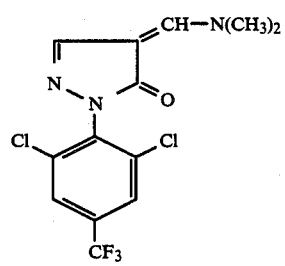

29.7 g (0.1 mol) of 1-(2,6-dichloro-4-trifluoromethylphenyl)-pyrazoline-5-one are suspended in 250 ml of toluene and treated with 13.1 g (0.11 mol) of dimethylformamide and dimethylacetal, resulting in a clear solution. The reaction mixture is stirred at room temperature for 16 hours. Once the reaction is definitely complete the batch is cooled to 0° C. and the precipitate suctioned off and dried in air.

The yield is 28.6 g (81% of the theoretical) of 1-(2,6-dichloro-4-trifluoromethylphenyl)-4-dimethylaminomethylene-Δ²-pyrazoline-5-one with a melting point of 220° C.

(b)

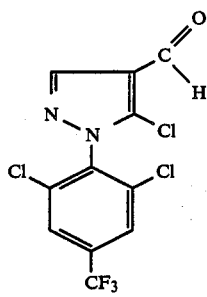

28 g (0.08 mol) of 1-(2,6-dichloro-4-trifluoromethylphenyl)-4-dimethylaminomethylene-Δ²-pyrazoline-5-one and 12.3 g (0.08 mol) of phosphorus oxychloride are stirred and heated to 100° C. for 8 hours. The product is cooled to room temperature and dissolved in 150 ml of methylene chloride and the organic phase washed twice with 100 ml of water and dried over sodium sulfate. The solvent is removed in the vacuum, the residue picked up in 250 ml of petroleum ether, and the insoluble components filtered out. Removing the solvent by vacuum results in 18.8 g (59% of the theoretical) of 1-(2,6)-dichloro-4-trifluoromethylphenyl)-4-formyl-5-chloropyrazole with a melting point of 58°-62° C.

(c)

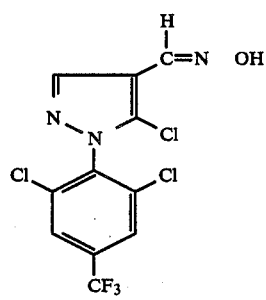

62.5 g (0.18 mol) of 1-(2,6-dichloro-4-trifluoromethylphenyl)-4-formyl-5-chloropyrazole and 13.7 g (0.2 mol) of hydroxylammonium chloride are dissolved in 800 ml of ethyl alcohol and heated to the reflux point for 3 hours. The batch is cooled to room temperature and poured over 4 l of water and the crystalline residue suctioned off. Drying under vacuum results in a yield of of 62 g (96% of the theoretical) of 1-(2,6-dichloro-4-trifluoromethylphenyl)-4-carbaldehyde-oxime-5-chloropyrazole with a melting point of 129°-135° C.

(d)

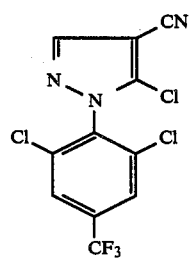

62 g (0.173 mol) of 1-(2,6-dichloro-4-trifluoromethylphenyl)-4-carbaldehyde-oxime-5-chloropyrazole are suspended in 90 ml of acetic anhydride and the reaction mixture heated to the point of reflux, resulting in a clear solution. The solution is heated under reflux for 3 more hours, cooled to room temperature, and the excess acetic anhydride distilled off under vacuum. The residual oil is crystallized by trituration. The solid is picked up in 500 ml of hot petroleum ether and left overnight at −20° C. The crystalline precipitate is suctioned off and air-dried.

The yield is 48.5 g (82% of the theoretical) of 1-(2,6-dichloro-4-trifluoromethylphenyl)-4-cyano-5-chloropyrazole with a melting point of 86°-87° C.

The following 1-aryl-4-cyano-5-halogenopyrazoles of the general formula (I) are obtained in a corresponding manner and according to the general preparation information:

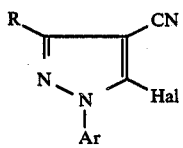

TABLE 2

| Example No. | R | Hal | Ar | Melting point/°C. |
|---|---|---|---|---|
| 3 | H | Br | 2,6-dichloro-4-SCF₃-phenyl | 95 |
| 4 | H | Cl | 2,4-dichloro-CF₃-phenyl | 68–72 |
| 5 | H | Br | 2-chloro-4-OCF₃-phenyl | 83 |
| 6 | H | Br | 2-chloro-4-CF₃-phenyl | 127 |
| 7 | H | Br | 2,6-dichloro-4-OCF₃-phenyl | 81 |
| 8 | H | Br | 2-chloro-4-SCF₃-phenyl | 137 |

TABLE 2-continued

| Example No. | R | Hal | Ar | Melting point/°C. |
|---|---|---|---|---|
| 9 | H | Br | 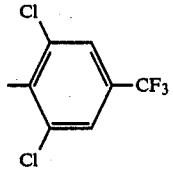 (2,4-Cl with CF3) | 92 |
| 10 | H | Br | 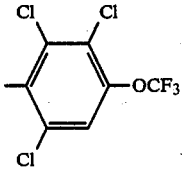 (2,4-Cl, OCF3, Cl) | 98-99 |

Use Examples

In the use examples below, the compound listed below was used as a comparative substance:

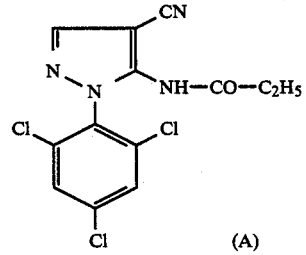

(disclosed in DE-OS (German Published Specification) No. 3,226,513)

Example A

Pre-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, a clearly superior selectivity in crop plants, especially in sugar-beet and corn compared with comparison substance (A), is shown e.g. by the compound according to preparation Example 6.

TABLE A

| Active compound | Amount of active compound kg/ha | Pre-emergence-Test/greenhouse | | | | | |
|---|---|---|---|---|---|---|---|
| | | Sugarbeets | Maize | Amaranthus | Purslane | Solanum | Sorghum |
| 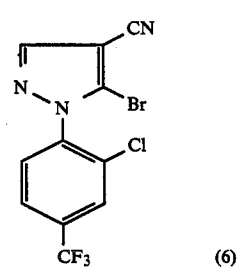 (A) | 0,5 | 100 | 100 | 100 | 100 | 100 | 100 |
| 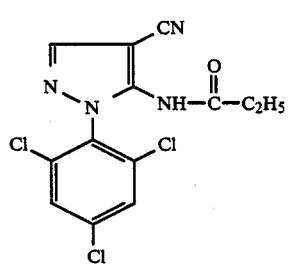 (6) | 0,5 | 0 | 20 | 100 | 100 | 100 | 95 |

Example B

Post-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied to 2,000 L of water/ha. After three weeks, the degree of damage to the plants is rated in % damage in comparison to the development of the untreated control. The figures denote:

0% = no action (like untreated control)
100% = total destruction

In this test, a clearly superior selectivity in crop plants, especially in soy beans and wheat compared with comparison substance (A), is shown e.g. by the compounds according to preparation Example 6.

emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of

TABLE B

| Active compound | Amount of active compound kg/ha | Soy | Wheat | Amaranthus | Ipomoea | Purslane | Setaria |
|---|---|---|---|---|---|---|---|
| 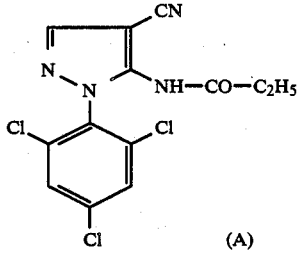 (A) | 0,5 | 100 | 50 | 100 | 100 | 100 | 100 |
| 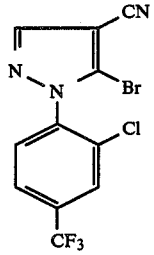 (6) | 0,5 | 40 | 20 | 100 | 100 | 100 | 100 |

Example C

Pre-emergence test / Greenhouse
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of damage to the plants is rated in % damage in comparison to the development of the untreated control. The figures denote:

0 % = no action (like untreated control)
100 % = total destruction

The active compounds, the amounts applied and the results obtained can be seen from Table C which follows:

TABLE C

| | pre-emergence-Test/greenhouse | | | | | |
|---|---|---|---|---|---|---|
| Active compound | Amount of active compound g/ha | result (%) cotton | Abutilon | Datura | Galinsoga | Setaria |
| 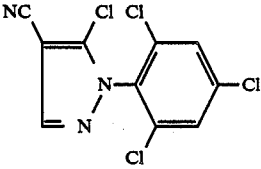 (known) | 500 | 0 | 0 | 0 | 0 | 20 |
| 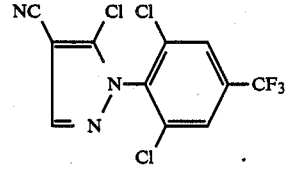 (Expl. 4) | 500 | 0 | 100 | 70 | 95 | 100 |

Example D

Post-emergence test / greenhouse
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way to apply the amounts of active compound per unit area which are indicated in the table. The concentration of the spray liquor is so chosen that the amounts of active compound shown in the table are applied in 2,000 l of water/ha. After three weeks, the degree of damage of the plants is rated in % damage in comparison with the development of the untreated control. The figures denote:

0%=no action (like untreated control)
100%=total destruction

The active compounds, amounts applied and results can be seen from the following Table D:

TABLE D

| Active compound | post-emergence-Test/greenhouse | | | | | | |
|---|---|---|---|---|---|---|---|
| | Amount of active compound g/ha | wheat | result (%) Datura | Ipomoea | Portulaca | Solanum | Setaria |
| 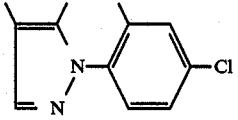 (known) | 250 | 0 | 10 | 50 | 40 | 50 | 0 |
| 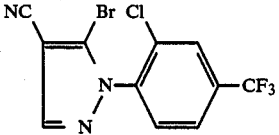 (Expl. 6) | 250 | 0 | 90 | 100 | 100 | 100 | 100 |

It will be understood that the specification and examples are illustrative but not limitative of the present invention and that other embodiments within the spirit and scope of the invention will suggest themselves to those skilled in the art.

We claim:

1. A 1-aryl-4-cyano-5-halogenopyrazole of the formula

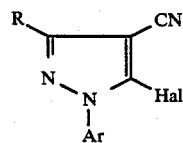

in which
R is hydrogen or alkyl having 1 to 4 carbon atoms,
Ar is phenyl which is substituted at least once by halogen and at least once by halogenoalkyl which has up to 4 carbon atoms and up to 9 halogen atoms, and
Hal is fluorine, chlorine, bromine or iodine.

2. A compound according to claim 1, in which
R is hydrogen, methyl or ethyl,
Hal represents fluorine, chlorine, bromine or iodine, and
Ar is phenyl which is substituted at least once by fluorine, chlorine, bromine or iodine, and at least once by trifluoromethyl, trichloromethyl, dichlorofluoromethyl, difluorochloromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl or pentachloroethyl.

3. A compound according to claim 1, wherein such compound is 5-bromo-4-cyano-1-(2-chloro-4-trifluoromethylphenyl)-pyrazole of the formula

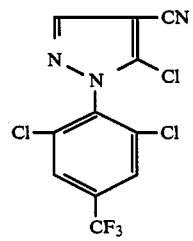

4. A compound according to claim 1, wherein such compound is 4-cyano-5-chloro-1-(2,6-dichloro-4-trifluoromethylphenyl)-pyrazole of the formula 5. A herbicidal composition comprising a herbicidally effective amount of a compound according to claim 1 in admixture with a diluent.

6. A method of combating unwanted vegetation which comprises applying to such vegetation or to a locus from which it is desired to exclude such vegetation a herbicidally effective amount of a compound according to claim 1.

7. The method according to claim 6, wherein such compound is
- 5-bromo-4-cyano-1-(2-chloro-4-trifluoromethylphenyl)-pyrazole, or
- 4-cyano-5-chloro-1-(2,6-dichloro-4-trifluoromethylphenyl)-pyrazole.

* * * * *

UNITED STATES PATENT AND TRADEMARK OFFICE
CERTIFICATE OF CORRECTION

PATENT NO. : 4,804,398

DATED : February 14, 1989

INVENTOR(S) : Reinhold Gehring, et al

It is certified that error appears in the above-identified patent and that said Letters Patent is hereby corrected as shown below:

| | |
|---|---|
| Col. 5, line 1 | Before "dichloroethoxy" insert --trifluoroethoxy, difluorodichloroethoxy, trifluoro- -- |
| Col. 15, line 20 | Delete "25020 C." and substitute --250° C.-- |
| Col. 15, line 63 | Before "cyclized" insert --are-- |
| Col. 16, line 31 | Delete "(VII)" and substitute --(VIII)-- |
| Col. 18, line 44 | Correct --Lindernia-- |
| Col. 19, line 60 | Correct --lignin-- |
| Col. 20, line 17 | Delete "or" second instance |
| Col. 23, line 30 | Upper right of formula delete "H ... C=N OH" and substitute --H ... C=N~OH-- |
| Col. 30, line 25 | Move formula above Table D |

Signed and Sealed this

Twenty-sixth Day of December, 1989

Attest:

JEFFREY M. SAMUELS

Attesting Officer    Acting Commissioner of Patents and Trademarks